(12) United States Patent
Iddan

(10) Patent No.: US 7,553,276 B2
(45) Date of Patent: Jun. 30, 2009

(54) METHOD AND DEVICE FOR IMAGING BODY LUMENS

(75) Inventor: Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 760 days.

(21) Appl. No.: 10/812,908

(22) Filed: Mar. 31, 2004

(65) Prior Publication Data

US 2005/0004474 A1    Jan. 6, 2005

Related U.S. Application Data

(63) Continuation-in-part of application No. 10/046,541, filed on Jan. 16, 2002.

(60) Provisional application No. 60/261,188, filed on Jan. 16, 2001, provisional application No. 60/458,438, filed on Mar. 31, 2003, provisional application No. 60/466,729, filed on May 1, 2003.

(51) Int. Cl.
*A61B 1/06* (2006.01)
*A61B 6/00* (2006.01)

(52) U.S. Cl. ...................... 600/160; 600/476

(58) Field of Classification Search ............... 600/407, 600/109, 476, 101, 300, 478; 348/74; 396/17
See application file for complete search history.

(56) References Cited

U.S. PATENT DOCUMENTS

| | | |
|---|---|---|
| 3,683,389 A | 8/1972 | Hollis |
| 3,971,362 A | 7/1976 | Pope et al. |
| 4,278,077 A | 7/1981 | Mizumoto |
| 4,588,294 A | 5/1986 | Siegmund |
| 4,689,621 A | 8/1987 | Kleinberg |
| 4,741,327 A | 5/1988 | Yabe |
| 4,844,076 A | 7/1989 | Lesho et al. |
| 4,951,135 A | 8/1990 | Sasagawa et al. |
| 5,279,607 A | 1/1994 | Schentag et al. |
| 5,381,784 A | 1/1995 | Adair |
| 5,459,605 A | 10/1995 | Kempf |

(Continued)

FOREIGN PATENT DOCUMENTS

DE    34 40 177    5/1986

(Continued)

OTHER PUBLICATIONS

The Radio Pill, Rowlands, et al., British Communications and Electronics, Aug. 1960, pp. 598-601.

(Continued)

*Primary Examiner*—Eric F Winakur
*Assistant Examiner*—Michael T Rozanski
(74) *Attorney, Agent, or Firm*—Pearl Cohen Zedek Latzer, LLP

(57) ABSTRACT

An in-vivo imaging device including a ballast that may for example orient such device in a known orientation relative to the gravitational force on such ballast. Such imaging device may, for example, assume a known orientation when it is free to move, and may capture images from such known orientation. The device may include one or more imagers, which may be oriented at different angles or points of view (e.g., forward and transverse). A method of use may include moving a patient so that the device inside the patient images different fields of view.

35 Claims, 7 Drawing Sheets

U.S. PATENT DOCUMENTS

| | | | |
|---|---|---|---|
| 5,603,687 | A | 2/1997 | Hori et al. |
| 5,604,531 | A | 2/1997 | Iddan et al. |
| 5,643,175 | A | 7/1997 | Adair |
| 5,819,736 | A | 10/1998 | Avny et al. |
| 5,833,603 | A * | 11/1998 | Kovacs et al. ............... 600/317 |
| 5,940,126 | A | 8/1999 | Kimura |
| 5,993,378 | A * | 11/1999 | Lemelson .................. 600/109 |
| 6,184,923 | B1 | 2/2001 | Miyazaki |
| 6,240,312 | B1 | 5/2001 | Alfano et al. |
| 6,709,387 | B1 * | 3/2004 | Glukhovsky et al. ........ 600/109 |
| 6,939,292 | B2 | 9/2005 | Mizuno |
| 7,009,634 | B2 * | 3/2006 | Iddan et al. .................. 348/76 |
| 7,039,453 | B2 * | 5/2006 | Mullick et al. .............. 600/476 |
| 2001/0017649 | A1 | 8/2001 | Yaron |
| 2001/0051766 | A1 | 12/2001 | Gazdzinski |
| 2002/0109774 | A1 | 8/2002 | Meron et al. |
| 2002/0198439 | A1 | 12/2002 | Mizuno |
| 2003/0018280 | A1 | 1/2003 | Lewkowicz et al. |
| 2003/0114742 | A1 | 6/2003 | Lewkowicz et al. |
| 2003/0120130 | A1 | 6/2003 | Glukhovsky et al. |
| 2003/0181788 | A1 * | 9/2003 | Yokoi et al. ................. 600/160 |

FOREIGN PATENT DOCUMENTS

| | | |
|---|---|---|
| EP | 0228493 | 3/1991 |
| JP | 57-45833 | 3/1982 |
| JP | 58-29439 | 2/1983 |
| JP | HEI 3-289779 | 12/1991 |
| JP | 4109927 | 4/1992 |
| JP | HEI 4-109927 | 4/1992 |
| JP | 1992-144533 | 5/1992 |
| JP | HEI 4-180736 | 6/1992 |
| JP | 5015515 | 1/1993 |
| JP | 2001224553 | 8/2001 |
| WO | WO 92/21307 | 12/1992 |
| WO | WO 96/37796 | 11/1996 |
| WO | WO 98/11816 | 3/1998 |
| WO | WO 98/51993 | 11/1998 |
| WO | WO 00/22975 | 4/2000 |
| WO | WO 00/76391 | 12/2000 |
| WO | WO 01/08548 | 2/2001 |
| WO | WO 01/50180 | 7/2001 |
| WO | WO 01/50941 | 7/2001 |
| WO | WO 01/65995 | 9/2001 |
| WO | WO 02/054932 | 7/2002 |
| WO | WO 02/094337 | 11/2002 |
| WO | PCT/IL03/00784 | 9/2003 |

OTHER PUBLICATIONS

Wellesley company sends body montiors into space—Crum, Apr. 1998.

Wireless transmission of a color television moving image from the stomach using a miniature CCD camera, light source and microwave transmitter• Swain CP, Gong F, Mills TN. Gastrointest Endosc 1997;45:AB40.

BBC News Online—Pill camera to 'broadcast from the gut', Feb. 21, 2000, www.news.bbc,co.uk.

Video Camera to "Take"—RF System lab, Dec. 25, 2001.

www.rfnorkia.com—NORIKA3, Dec. 24, 2001.

U.S. Appl. No. 10/213,345, filed Aug. 7, 2002, Glukhovsky.

Wang, et al., "Integrated Micro-Instrumentation for Dynamic Monitoring of the Gastro-Intestinal Tract", Presented at IEEE Instrumentatioin and Measurement Technology Conference, May 2002, Anchorage, Ak, USA, www.see.ed.ac.uk/Naa.publications.html.

Dan Slater, Panoramic Photography with Fisheye Lenses, © 1995, Published in IAPP Journal, 1996.

* cited by examiner

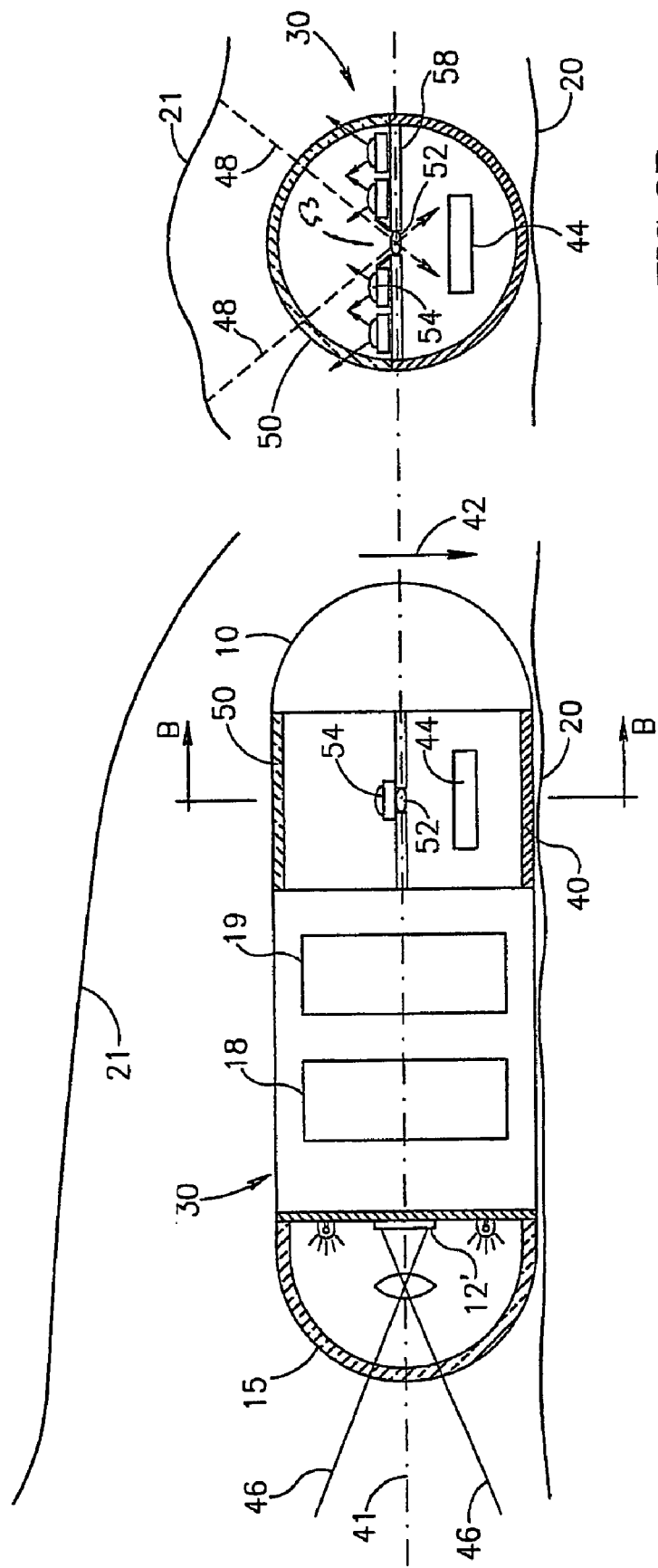

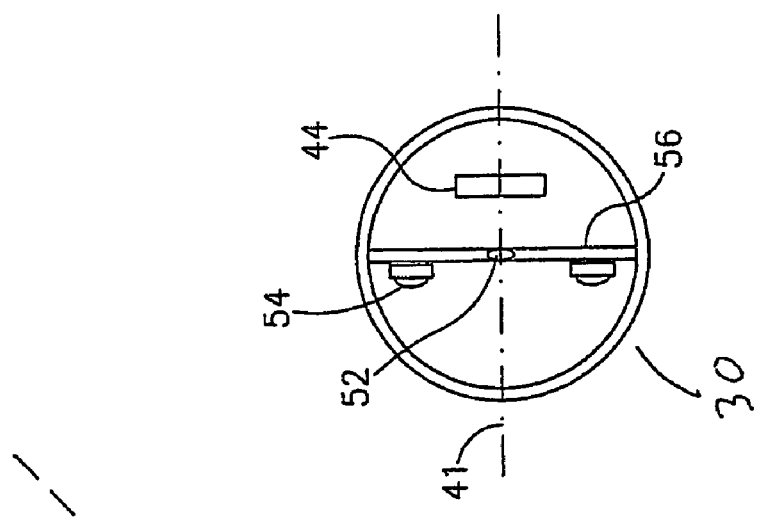
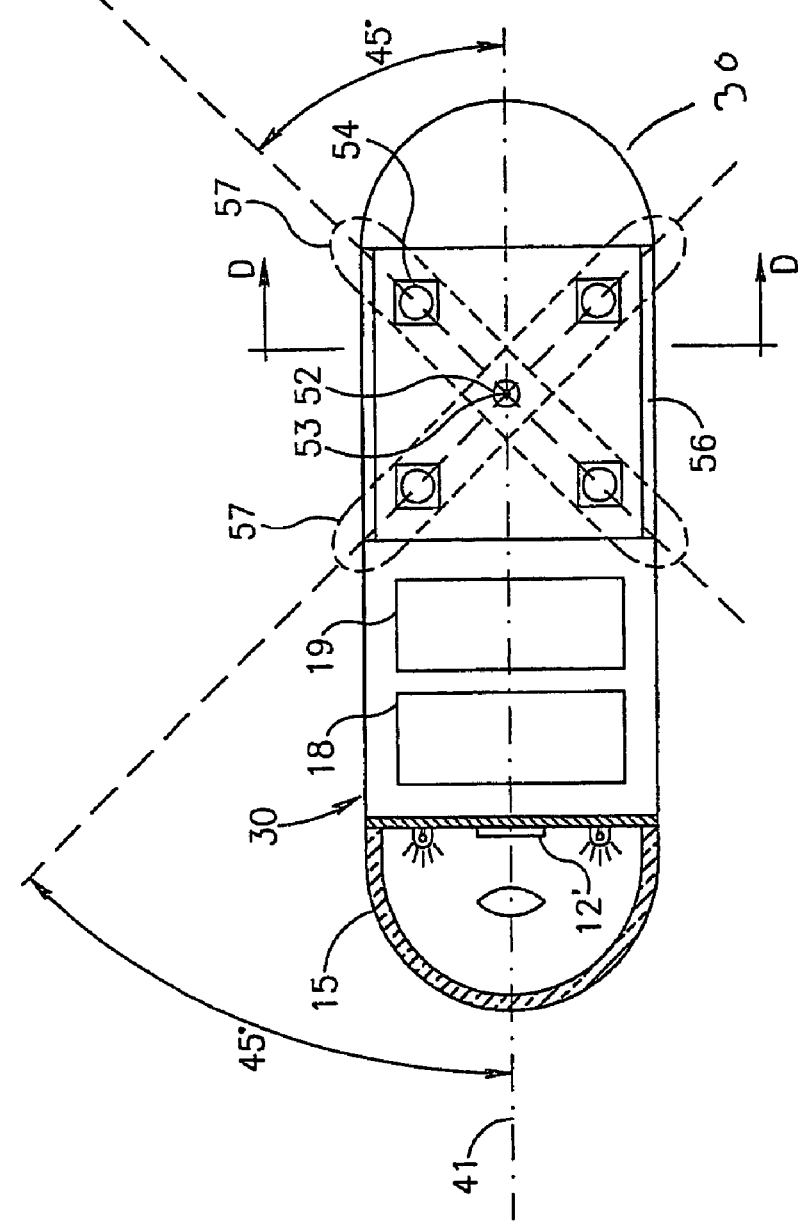

METHOD AND DEVICE FOR IMAGING BODY LUMENS

CROSS REFERENCE TO RELATED APPLICATIONS

This application claims benefit from U.S. provisional application Ser. No. 60/458,438, filed on Mar. 31, 2003, which is incorporated in its entirety by reference herein and U.S. provisional application Ser. No. 60/466,729 filed May 1, 2003, which is incorporated in its entirety by reference herein. This application is also a continuation-in-part of prior U.S. patent application Ser. No. 10/046,541 filed on Jan. 16, 2002 entitled System and Method for Wide Field Imaging of Body Lumens, which is incorporated in its entirety by reference herein, and which claims benefit of prior provisional application 60/261,188 filed on Jan. 16, 2001.

FIELD OF THE INVENTION

The present invention relates to the field of in vivo diagnostics. More specifically, the present invention relates to a method for sensing, for example, imaging, body lumens.

BACKGROUND OF THE INVENTION

Some pathologies of the gastrointestinal (GI) tract, involve epithelial damage, erosions, and ulcers. For example, inflammation of the GI tract mucosa (typically in the stomach), such as gastritis, can be characterized, inter alia, based on the endoscopic appearance of the gastric mucosa (e.g., varioliform gastritis). Other pathologies may involve irregularities or abnormal appearances of folds, polyps or color indications (such as bleeding) on the GI tract wall. Detection of these pathologies at an initial stage plays an important role in enhancing the probability of a cure.

Screening populations for initial signs of GI tract pathologies is typically carried out by non-invasive methods including x-ray images in which a patient intakes x-ray opaque (radio-opaque) material (barium, gastrographine, or others). The material resides for some time on the walls of the GI tract, enabling examination of the x-ray images of the GI-tract. This technique has several drawbacks, namely, low detection rate and exposure to x-ray radiation. Other screening methods include viewing the GI tract walls or lumens by means of appropriate endoscopes. For example, flexible upper endoscopy is often performed to evaluate for a gastrointestinal etiology of pain such as mucosal inflammation (esophagitis, gastritis, duodenitis), ulceration, or a neoplasm. Risks associated with flexible upper endoscopy include injury to the bowel wall, bleeding, and aspiration. Upper endoscopy is usually performed under conscious sedation, which carries risks as well. Furthermore, patients typically need to take a day off of normal activities due to the lasting effects of conscious sedation. Finally, the endoscopy procedure is clearly a cause of discomfort, pain and vomiting in many patients. Even the physical dimensions of the endoscope can be a cause for fear. Such risks, along with the prospect of incapacitation and fear, are often used as justifications by patients for delaying or altogether avoiding gastroscopic diagnosis.

Visualization of the GI tract, including the more difficult to reach areas, such as the small intestine, is possible today using an ingestible imaging capsule. Images of the GI tract are obtained by a miniature image sensor carried by the capsule and are transmitted to an external recorder to be later viewed on a workstation. Sensing other parameters of the GI tract, such as pH or temperature, are also possible by using ingestible transmitting capsules. Ingestible capsules may be moved through the GI tract by the natural movement of peristalsis. However, in larger or voluminous lumens, such as the stomach or large intestine, the view or sensing capacity of a capsule may not cover the entire surface of the lumen wall.

SUMMARY OF THE INVENTION

According to an embodiment of the invention a method and device are provided for imaging in-vivo areas or body lumens by including in an in-vivo device an imager or image sensor and a ballast. A ballast may in some embodiments be a component or part of the in-vivo device that may be weighted or otherwise situated so that the center of gravity of the in-vivo device is towards a particular side of the in-vivo device. In some embodiments, a ballast may orient the in-vivo device in a known orientation. For example, a ballast may create a center of gravity of the in-vivo device that is below a longitudinal axis of symmetry of the in-vivo device so that gravity pulls the ballast to a point below such axis of symmetry. The ballast may be configured to reorient the in-vivo device in response to a rotation or other movement of a body in which the in-vivo device is located, or for example in response to a magnetic field. In some embodiments, an optical system may be located on a transverse portion, or long side and at a horizontal orientation, of an outer shell of the in-vivo device and in a diametrically opposite position to the ballast. In some embodiments, when the ballast may be oriented to a downward facing position, an optical system may be in an upward facing position. In some embodiments an optical system along a transverse side may be oriented so that it is in a downward facing position when the ballast is oriented below the axis of symmetry of the device.

The optical system may be configured to collect light reflected from a wide angle of an in-vivo area. In some embodiments the optical system may include a magnifying device. In some embodiments a second optical system may be situated on an axial end, such as for example a front or back end, of the in-vivo device. The device may be configured to collect light reflected from a wide angle of an in vivo area.

The device may for example include a curved mirror that may direct light reflected from a circular field of view of an in-vivo area surrounding the transverse portion of the in-vivo device. The device may be configured to collect light reflected off a ring shaped slice of an in-vivo area.

A method of an embodiment of the invention may include capturing with an autonomous in-vivo imaging device a first image of a first in-vivo area that is in front of an axial plane of the device, and capturing with such imaging device a second image of a second in-vivo area, which is transverse to the axial plan of the device.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof may best be understood by reference to the following detailed description when read with the accompanying drawings in which:

FIG. 2A is a schematic illustration of a capsule, constructed and operative in accordance with an embodiment of the present invention, within a voluminous lumen;

FIG. 2B is a cross-sectional illustration of the capsule of FIG. 2A, taken along lines B-B of FIG. 2A in accordance with an embodiment of the invention;

FIG. 2C is a schematic illustration of an alternative embodiment of the capsule of FIG. 2A in accordance with an embodiment of the invention;

FIG. 2D is a cross-sectional illustration of the capsule of FIG. 2C, taken along lines D-D of FIG. 2C in accordance with an embodiment of the invention;

Figure 1A:
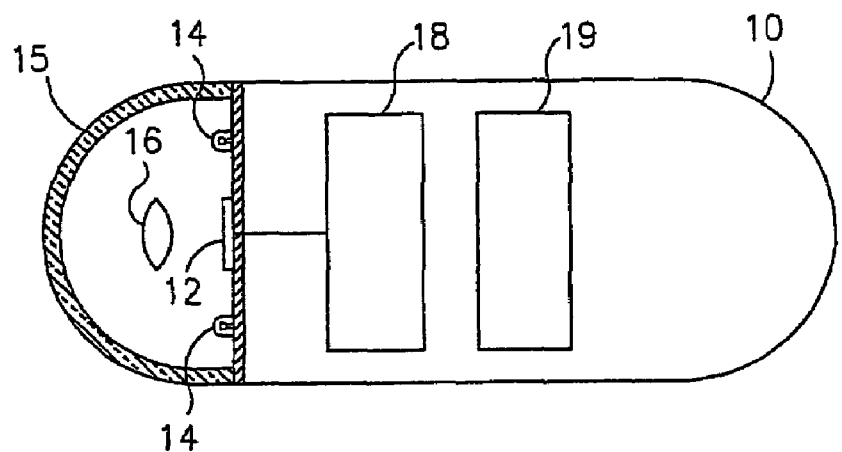
FIG. 1A is a schematic illustration of a capsule.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Reference is now made to FIG. 1A, which illustrates an ingestible device 10, which may be, for example, a capsule, but which may have other shapes or configurations. Device 10 may be, for example, similar to embodiments described in U.S. Pat. No. 5,604,531 to Iddan et al., and/or WO 01/65995, entitled "A Device And System For In Vivo Imaging", published on 13 Sep., 2001, both of which are assigned to the common assignee of the present invention and which are hereby incorporated by reference. However, device 10 may be any sort of in-vivo sensor device and may have other configurations.

Device 10 typically includes an imager or image sensor 12, such as a charged coupled device (CCD) or complementary metal oxide semiconductor (CMOS) imager, one or more illumination sources 14, such as an LED, a window 15 and an optical system 16, shown schematically as a lens, for focusing images onto the image sensor 12. Other items such as for example a lens holder may also be included in optical system 16. Device 10 may further include a transmitter 18 and a battery 19.

Transmitter 18 may be an ultra low power radio frequency (RF) transmitter with high bandwidth input, possibly provided in chip scale packaging. The transmitter 18 may also include circuitry and functionality for controlling the device.

The transmitter may be, for example, an ASIC, "computer on a chip", microcontroller, etc., or other component. Components such as the image sensor, illumination source and transmitter may be mounted on a support, which may be, for example, a printed circuit board or plastic board or sheet. The support may be another structure, and components need not be mounted on a separate support. Other components may also be included in device 10.

An autonomous, ingestible imaging capsule, such as device 10 or any other suitable imaging capsule, may be inserted into a body lumen and a patient may be positioned in such a way so as to achieve corresponding positioning of the capsule within the patient's body lumen. For example, device 10 may be utilized for screening the walls of the stomach by having a patient swallow device 10 and then positioning the patient, for example, on a rotating bed such as for example a TOSHIBA ULTIMAX rotating bed in order to move the capsule along the patient's stomach wall. However, other body lumens or cavities may be imaged or examined, and the device need not be ingestible. For example, a device may be inserted into the female reproductive tract or urinary tract for obtaining in-vivo data.

Figure 1B:
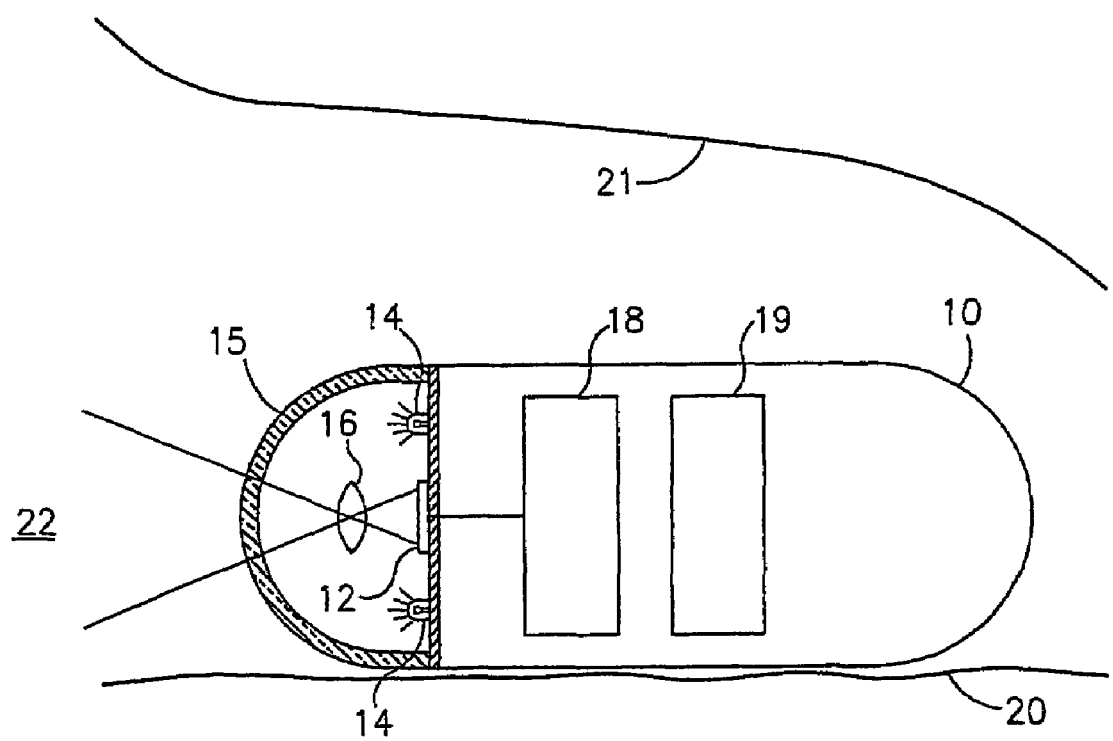
FIG. 1B is a schematic illustration of the capsule of FIG. 1A within a voluminous lumen.

Reference is now made to FIG. 1B, which shows device 10 in a large body lumen. Device 10 is shown against a wall 20 of a large lumen, such as the stomach. Imager 12 may view the space in front of device 10, which, in FIG. 1B, is open space, labeled 22. In one configuration, only a very small portion of imager 12 views a portion of wall 20; most of imager 12 views open space 22. Thus, although device 10 may image wall 20 as it may be moved along wall 20, and may image wall 21 as it may be moved along wall 21, a large portion of the images produced may not contain useful information, as they may have imaged open space 22.

Reference is now made to FIGS. 2A and 2B, which together illustrate a device 30, constructed and operative in accordance with an embodiment of the present invention. Device 30 may be, for example, a capsule, but may have other shapes or configurations. FIG. 2A shows a side view and FIG. 2B shows a cross-sectional view. Device 30 may be similar to device 10 in some respects and thus, similar reference numerals refer to similar elements.

Device 30 typically may be or may include an autonomous swallowable capsule, but device 30 may have other shapes and need not be swallowable or autonomous. Embodiments of device 30 are typically self-contained. For example, device 30 may be a capsule or other unit where all the components are substantially contained within a container or shell, and where device 30 does not require any wires or cables to, for example, receive power or transmit information. Device 30 may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

In accordance with an embodiment of the present invention, device 30 may include one or more ballast(s) 40 which may provide orientation to device 30. Reference to ballast 40 may define a "downward" direction, as indicated by arrow 42, for device 30 whenever device 30 is free to rotate, such as within a large or voluminous lumen. Accordingly, device 30 may fall or rotate or be oriented towards whichever wall 20 or 21 of the large lumen is gravitationally lower, and may fall such that ballast 40 may be close to the lower wall. Device 30 may thereby come to rest in a known orientation relative to the pull of gravitational force on ballast 40.

Ballast 40 may be made of any material which will provide device 30 or a portion of device 30 with a specific gravity larger than 1 or approximately 1, such that device 30 will fall in the direction of gravity, and be of a size and shape to ensure that the center of gravity of device 30 is below its longitudinal axis 41 of symmetry, such that device 30 may come to rest with ballast 40 near the lower wall. For example, for a capsule, which is 11 mm in diameter and 26 mm in length, ballast 40 may be made of 4.8 g of Tungsten and may be located below axis 41, generally in the midsection of device 30. Other weights and materials may be used for a ballast 40 or weight, and a ballast 40 or weight may have other configurations. For example, one or more separate units may be used for such a ballast 40 or weight. In some embodiments, ballast 40 may be or include an active component of device 30 such as for example transmitter 18 or a battery 19 or other component that may also serve a functional role in the operation of device 30. The placement of one or more components of device 30 for example towards or away from a longitudinal axis 41 of symmetry of device 30 may be sufficient for such components to serve as a ballast 40.

In accordance with an embodiment of the present invention, device 30 may also include more than one imager. The imagers may be oriented at different angles or points of view (e.g., forward and transverse). For example a forward looking imager 12' and an upward looking imager 44. Forward looking imager 12' may view or capture images of areas in the forward or backward direction (forward and backward possibly being relative and interchangeable terms, as an oblong device may have unpredictable orientation when inserted), such that its view may be from an axial end of device 30, as indicated by rays 46. A second imager 44 may be situated on a transverse portion, or long side, of device 30 such that its view may be towards an upward or downward angle from device 30, and that it may capture images along a direction that is parallel to the transverse portion of the device 30. An optical system 52 of upward looking imager 44 may be part of an outer shell or wall of device 30, and may view in an "upward" direction, as indicated by rays 48, opposite to downward direction 42 defined by ballast 40. For example, in FIG. 2A, imager 44 looks upward from the lower wall, wall 20, to the opposite, "upper" wall 21. Other directions may be used for each imager. Upward and downward may be interchangeable and relative terms, depending on the intended or actual orientation of a device.

Upward looking imager 44 may be any type of appropriate imager, such as one of the same or a different type as forward looking imager 12'. Device 30 may also include a second window 50, a second optical system 52, shown schematically as a lens, and a second illumination system 54, all operative with imager 44. Such second imaging components may share the same power source, control system, and transmitter as a first set of imaging components. Further, more than two sets of imaging components may be used.

According to another embodiment, window 50 and illumination system 54 may be configured to reduce backscatter of light. For example, window 50 may be ellipsoid shaped, similarly to window 15 (FIG. 1A) and/or as described in embodiments of PCT patent application published as WO 00/76391 published on Dec. 21, 2000, which is assigned to the common assignee of the present invention and which is hereby incorporated by reference.

Alternatively, and as shown in FIGS. 2A and 2B, window 50 may form part of the outer wall of device 30 and thus, may fit the cylindrical shape of device 30. In this embodiment, optical system 52 may be a lens, located at a center 53 of the cylinder of device 30 and imager 44 may be located below center 53, at an appropriate back focal length. Thus, only radial, or approximately radial rays, may be captured by lens 52. Non-radial rays generally are not captured in such a configuration. As long as illumination system 54 generates only non-radial rays, none of these rays may enter lens 52.

In the embodiment of FIGS. 2A and 2B, illumination system 54 includes four light sources mounted on a baffle 58 located along the diameter of the cylinder. However, none of the light sources are at center 53. Thus, minimal amounts, if any, of its rays may be focused onto imager 44. Other number of illumination units may be used, and such illumination units may assume other configurations.

Reference is now made to FIGS. 2C and 2D, which provide a further embodiment of device 30 in top and cross-sectional views, respectively. In FIGS. 2C and 2D, light sources 54 are mounted on baffle 58 at the foci of the ellipses 57 formed by cutting the cylinder by a plane tilted by 45 degrees from axis 41. Rays emitted from one focus of an ellipse pass to the other focus and do not arrive at the center of the ellipse (where lens 52 is mounted).

In accordance with an embodiment of the present invention, both imagers may operate at the same time. The two imagers may provide two different views of the lumen, shifted in time. Images may be activated or may capture or transmit images serially, in an interleaved fashion, sequentially or concurrently. Suitable transmission systems may be included, such as a system alternating transmitting images from each of two imagers (or more imagers); transmitting two or more images at the same time, etc.

In accordance with a second embodiment of the present invention, the imagers may be operated separately, during separate periods of operation as opposed to serially or interleaved, with imager 12' being operative for small, typically restricted lumens, and imager 44 being operative for large, typically voluminous lumens. For example, in the gastrointestinal tract, imager 12' may be operative during passage through the esophagus and/or small intestine while imager 44 may be operative during passage through the stomach and/or large intestine.

Embodiments of an imaging device with a plurality of imagers and its operation are described in WO 02/054932 published on Jul. 18, 2002 which is assigned to the common assignee of the present application and which is hereby incorporated by reference.

Reference is now made to FIGS. 3A, 3B, 3C and 3D, which illustrate device 30 during an exemplary screening of a stomach 60. During the screening, the patient may be rotated or otherwise moved about, such that device 30 may fall on many different portions of the wall of the stomach.

Figure 3A:
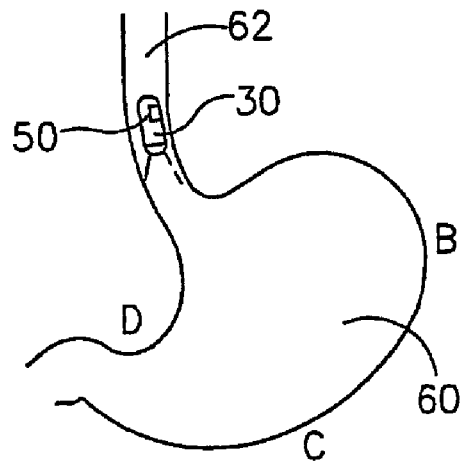
FIGS. 3A, 3B, 3C and 3D are schematic illustrations of the capsule of FIG. 2A in four exemplary locations within the esophagus and stomach in accordance with an embodiment of the invention.
Figure 3B:
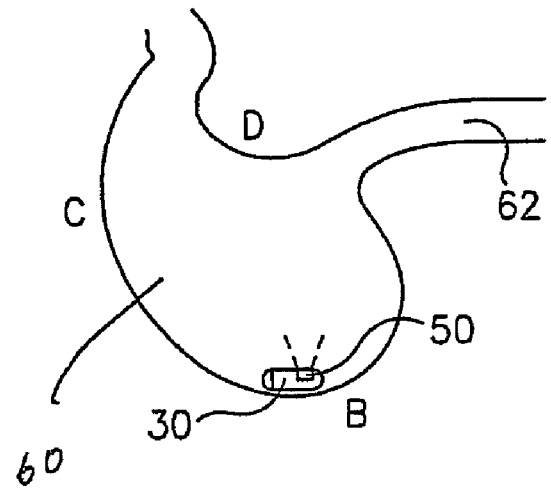
Figure 3C:
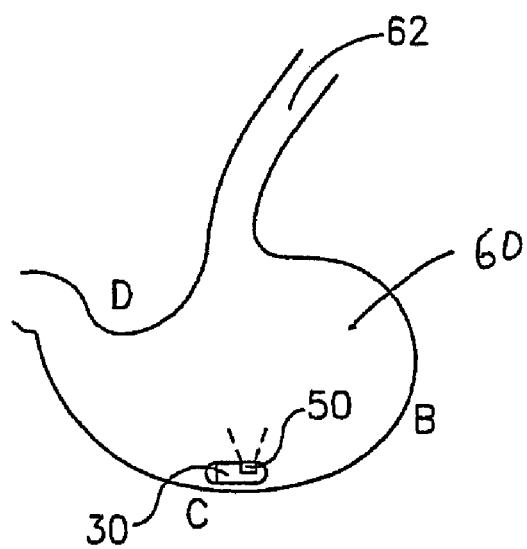
Figure 3D:
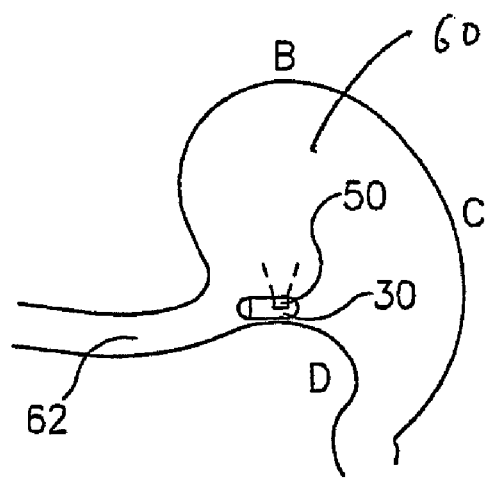

In FIGS. 3A-3D, four locations are shown, one within esophagus 62, and three, labeled B, C and D, within stomach 60. FIG. 3A shows device 30 within esophagus 62, and FIGS. 3B, 3C and 3D show device 30 at locations B, C and D, respectively. In FIG. 3A, device 30 is within the tight confines of esophagus 62 and thus, faces downward, in the direction of swallowing. However, once in stomach 60, device 30 is free to rotate or otherwise move. Initially, it falls toward location B and thus, can image location D. The patient is then rotated or otherwise moved and device 30 falls toward location C, roughly opposite to esophagus 62. Imager 44 is thus able to image the walls of esophagus 62 where they connect to the walls of stomach 60. The patient may then be rotated and device 30 may full toward location D and thus, may image location B. Other sequences of movement may be used.

Figure 4:
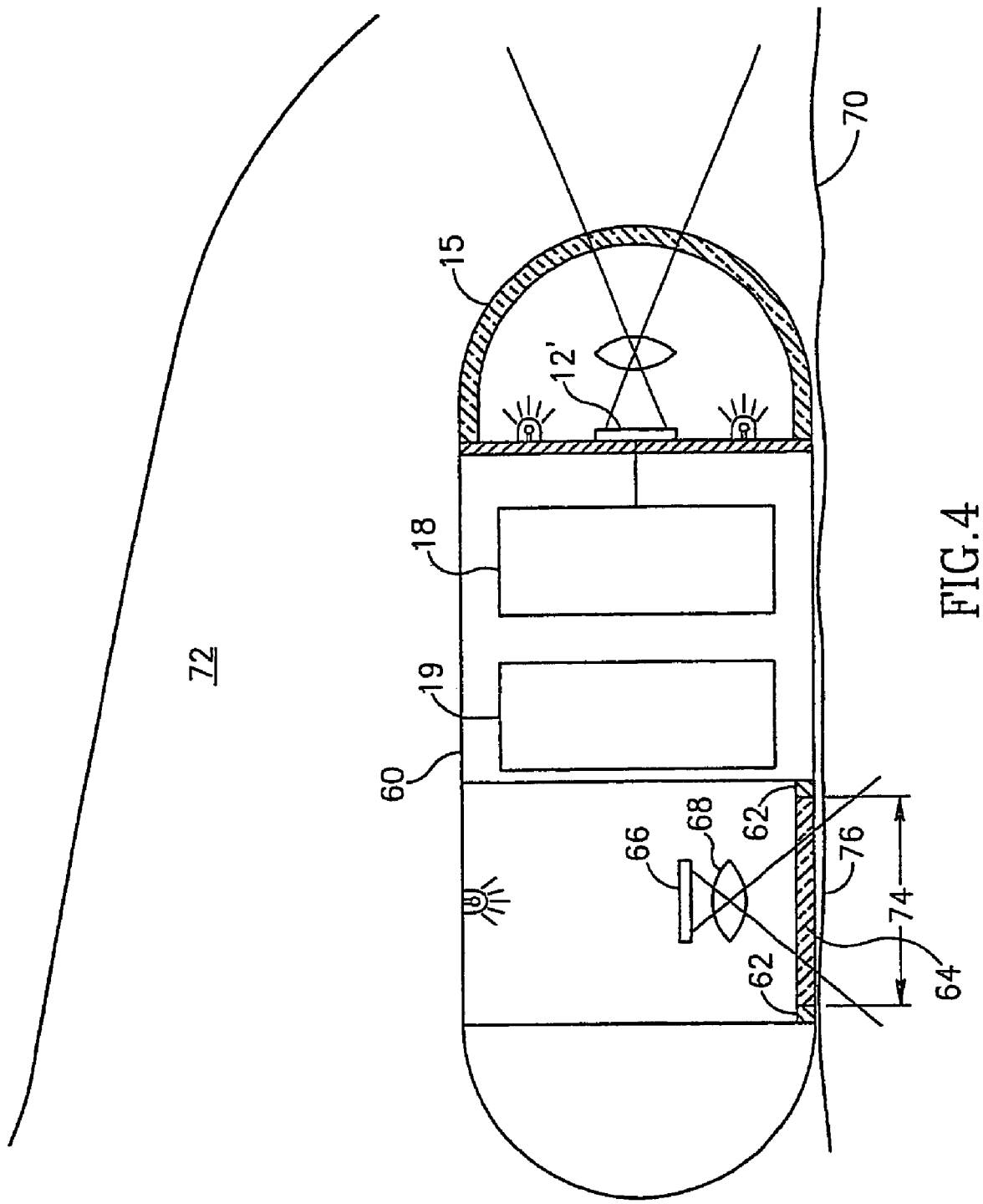
FIG. 4 is a schematic illustration of an alternative capsule, constructed and operative in accordance with an embodiment of the present invention.

Reference is now made to FIG. 4, which illustrates an optical biopsy device 60, constricted and operative in accordance with an embodiment of the present invention. Device 60 may be similar to device 30 in some respects and thus, similar reference numerals refer to similar elements.

Figure 5:
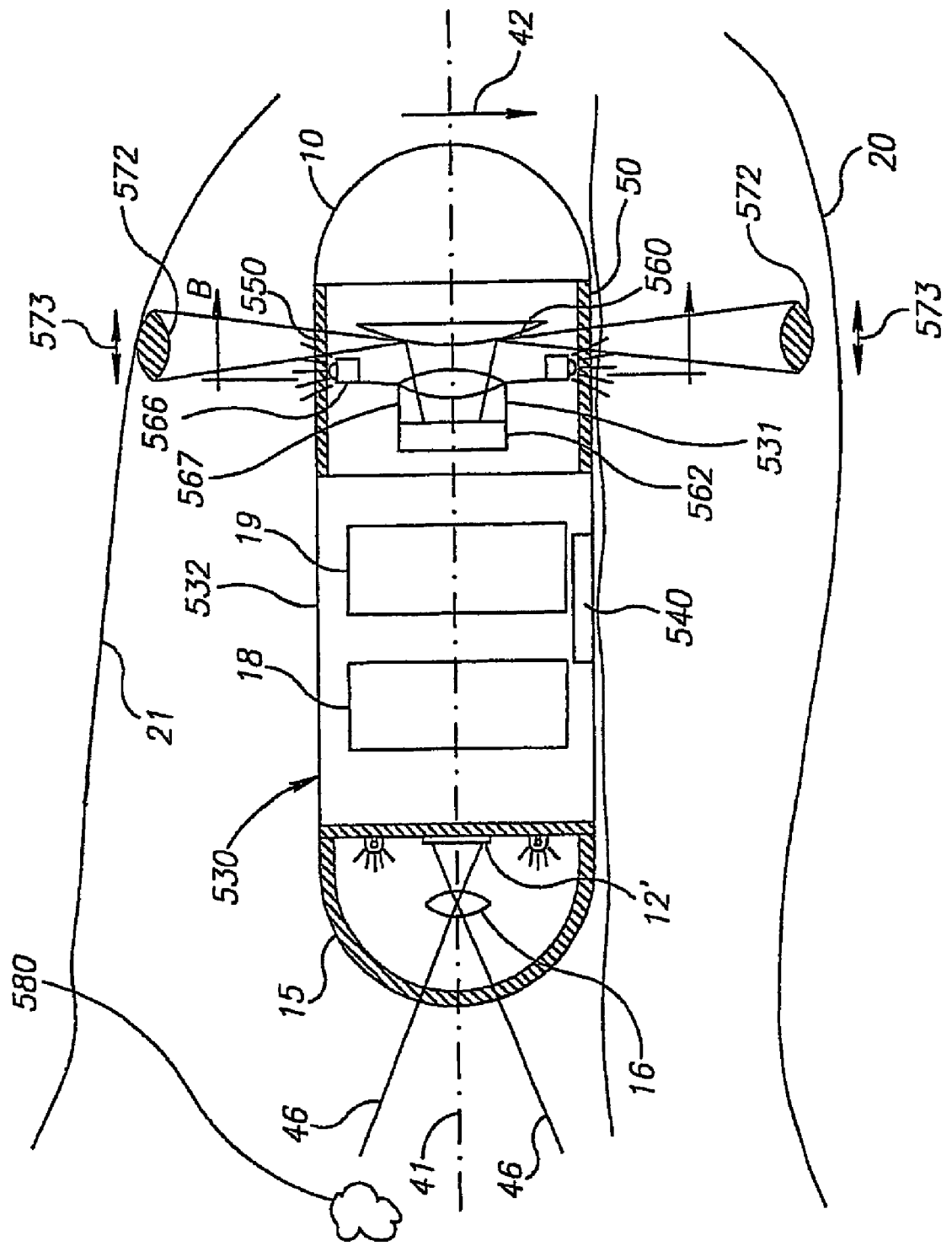
FIG. 5 is a schematic illustration of an in-vivo imaging device including a reflective element in accordance with embodiments of the invention.

In this embodiment, device 60 may include one or more ballast(s) 62 positioned around a downward looking window 64, an optical biopsy imager 66 looking through downward looking window 64 and a magnifying optical system 68, shown schematically as a lens. With ballast 62 around window 64, device 60 may fall with imager 66 looking downward at a wall 70 of a large lumen 72. Imager 66 may then image, in detail, a section 74 of wall 70. In FIG. 5, section 74 contains a pathology 76 which imager 66 may view.

In accordance with an embodiment of the present invention, imager 66 may operate as a microscope or a magnifying lens, providing magnification of section 74, in-vivo, such that a physician may be able to "take a biopsy" internally, rather than having to surgically remove the pathological element in order to view it. The amount of magnification may be a function of the size of the pixels in imager 66 and the optical qualities of optical system 68.

Any suitable method may be utilized to move device 60 to view a known pathology. In some cases, device 60 may be utilized during a screening operation and may be utilized to magnify pathologies it finds.

Further alternatively, device 60 may include a maneuvering unit (not shown), which enables the physician to maneuver capsule 60 to a desired location. One known type of maneuvering unit may be a magnet inside of device 60 and a magnetic unit placeable externally on a patient's body. Another maneuvering unit may be a motor and a propeller similar to embodiments described in U.S. patent application Ser. No. 10/212,139 filed on Aug. 6, 2002 entitled "System and Method For Maneuvering a Device In-Vivo", assigned to the assignee of this application and incorporated herein by reference, and in U.S. patent application Ser. No. 10/252,826 filed on Sep. 24, 2002 entitled "System and Method for Controlling a Device In-Vivo", assigned to the assignee of this application and incorporated herein by reference.

Reference is made to FIG. 5, a schematic illustration of an in-vivo imaging device including a curved reflective element and a ballast in accordance with an embodiment of the invention. Device 530 may in some embodiments be configured to be swallowed by a patient or otherwise introduced into a body lumen such as the GI tract, and may include a forward-viewing optical system 16 and a transverse viewing optical system 531. Device 530 may also include one or more ballast(s) 540. Ballast 540 may be capable of orienting device 530 in a known position relative to the gravitational force exerted against ballast 540.

Optical system 531 may include a reflective element 560, such as for example a curved mirror to capture a panoramic image of an in-vivo area parallel to a transverse side 532 of device 530. Device 530 may include a transparent area along a shell or outside of the device 530 that may in some embodiments be in the shape of a transparent ring 550 along or constituting part of a circumference of the transverse side 532 of device 530. Shapes other than a ring may be used. For example, a transparent area in the shape of a half circle or smaller arc of an outside portion of transverse side 532 may be used. Inside of ring 550 may be included optical system 531 which may include components such as a lens, a lens holder 567, one or more illumination elements 566 that may illuminate an in-vivo area and other components. An imager 562 may collect light reflected through optical system 564. Imager 562 may include an electronic imager for capturing images. For example, imager 562 may include a CMOS electronic imager including a plurality of elements. In embodiments of the invention, imager 562 may include other suitable types of optical sensors and/or devices able to capture images, such as a CCD, a light-sensitive integrated circuit, a digital still camera, a digital video camera, or the like.

Optical system 531 may allow imager 562 to capture an image of for example an object 572 that may be located on for example wall 21 or 20 as such image is reflected by curved mirror or other reflective element 560. In some embodiments, reflective element 560 may have a shape, size and/or dimensions to allow a desired reflection of light and/or to allow a desired range and/or field-of-view. In one embodiment, reflective element 260 may be manufactured using suitable optical design software and/or ray-tracing software, for example, using "ZEMAX Optical Design Program" software. In some embodiments, optical system 531 may include a lens or other device that may magnify an image.

In some embodiments, illumination source 566 may create a desired illumination, for example, homogenous illumination, of an imaged body lumen. Holder 567 may include a suitable structure to hold illumination sources 566. In some embodiments, holder 567 may be formed and/or shaped such that it reduces glare. In some embodiments, holder 567 may be formed and/or shaped such that it blocks stray light from reaching and/or flooding imager 562.

In one embodiment, as device 530 traverses a body lumen, device 530 may capture images of a slice of body lumen, such as the slice marked by arrow 573. Illumination source 566 may illuminate slice 573 of a body-lumen. The light from illuminated slice 573 may be reflected by a reflective element 560, and directed focused and/or transferred by lens 566. Light may be received by imager 562 which may capture an image of slice 573. In an embodiment, since device 530 may include transparent areas and/or portions, such as transparent ring 550, the captured image may include a reflected image of a circular field of view or ring-shaped slice 573 of wall 21 and 20 or of another area surrounding a transverse side 532 of device 530. It is noted that lens 566 may be configured, placed and/or aligned to filter and/focus light such that only light from a desired portion of wall 20 or 21, for example, a ring-shaped slice 573, falls on imager 562. Device 530 may allow, for example, capturing a panoramic image of slice 573 of wall 20 or 21 or another body lumen. Such panoramic image may include a substantially complete 360 degrees image of slice 573. If desired, such image may include a non-complete image of slice 573, for example, a 270 degrees image, a 210 degrees image, a 180 degrees image, or any other number of degrees between 0 and 360. Device 530 may also include a forward looking optical system 15 that may direct light reflected from an object 580 or in-vivo area that may be in front of or behind device 530.

In some embodiments, images captured by first optical system 16 which may face in a horizontal direction, and images captured by second optical system 531 which may face for example in a vertical direction may be transmitted by transmitter 18 concurrently or one after the other. In some embodiments, images from first optical system 16 and second optical system 531 may be transmitted by one or more transmitters 18 over a single channel or over more than one channel to an external receiver.

Figure 6:
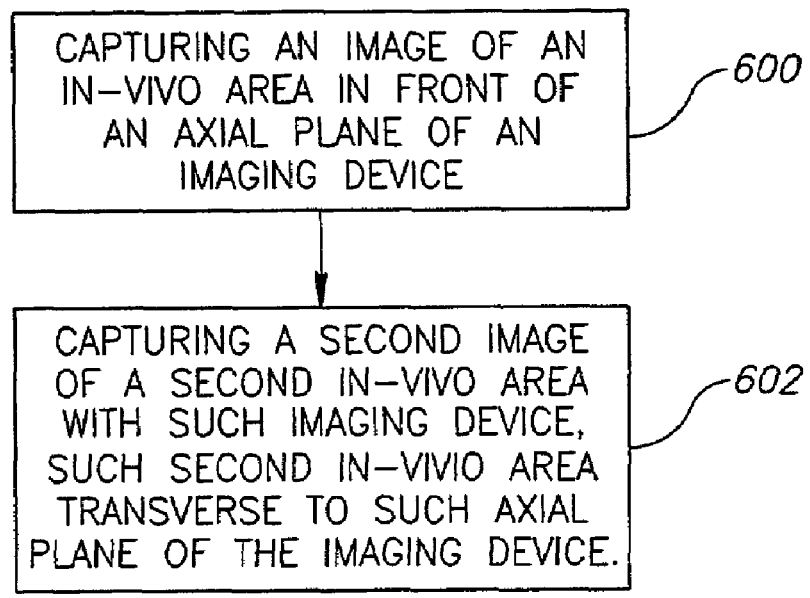
FIG. 6 is flow chart of a method of capturing images of in-vivo areas in accordance with an embodiment of the invention.
Figure 7:
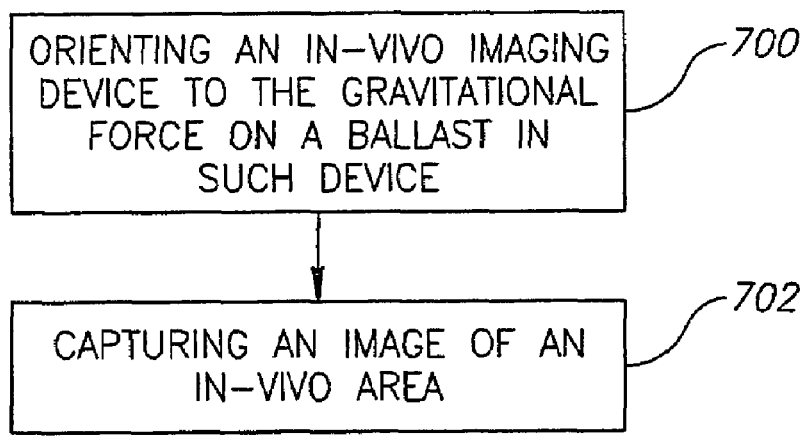
FIG. 7 is a flow chart of a method of orienting an in-vivo imaging device in accordance with an embodiment of the invention.

Reference is made to FIG. 6 a flow chart of a method in accordance with an embodiment of the invention. In block 600, an image is captured of a first in-vivo area in front of or behind an axial plane of an autonomous imaging device. In block 602, an image is captured with such imaging device of a second in-vivo area that is transverse to such axial plane of the in-vivo imaging device. Other operations or series of operations may be used.

In some embodiments, the image captured of the second in-vivo area may be or include a panoramic view, partially panoramic view or view of a ring shaped portion of the in-vivo area. In some embodiments on or more of the images may include a magnified image of a portion of the in-vivo area. Light that is captured by the image sensor may be reflected off of a curved reflective element that may reflect such light onto a lens. The image sensor may include a ballast that may be situated below a longitudinal axis of symmetry of the device, and the ballast may orient the imaging device in a known orientation relative to the gravitational force on the ballast. The ballast may be configured to move or reorient the device in response to a rotation or other movement of the body within which the device is located.

Reference is made to FIG. 1, a flow chart of a method of orienting an in-vivo imaging device in accordance with an embodiment of the invention. In block 700 an in-vivo device may be oriented into a known position by the gravitational force exerted on a ballast that may be included in the device. The ballast which, may be situated below a longitudinal axis of symmetry of the device, may cause the device to come to rest. With the ballast facing downward. In block 702 an image may be captured by for example an imager that is in a known position relative to the ballast. Other operations or series of operations may be used.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

I claim:

1. An autonomous in-vivo device comprising:
a housing having a longitudinal axis of symmetry:
an image sensor positioned in said housing to acquire images through a window in said housing; and
a ballast located off the longitudinal axis of symmetry, so that said device has a center of gravity displaced from the longitudinal axis of symmetry toward said window, such that the device rests in a known orientation.

2. The device as in claim 1, comprising an optical system located on a transverse side of said in-vivo device displaced from said longitudinal axis of symmetry.

3. The device as in claim 2, comprising an optical system on an axial portion of said device.

4. The device as in claim 2, wherein an outer shell of said device comprises said optical system.

5. The device as in claim 2, wherein said optical system comprises a magnifying device.

6. The device as in claim 2, wherein said optical system is configured to collect light reflected from a wide angle of said in-vivo area.

7. The device of claim 2, wherein said optical system is directed to capture an image of an in vivo area perpendicular to said longitudinal axis of symmetry.

8. The device as in claim 1, wherein said ballast is configured to re-orient said in vivo device in response to a movement of a body within which said in-vivo device is located.

9. The device as in claim 1, wherein said ballast is configured to change an orientation of said device in response to a magnetic field.

10. The device as in claim 1, wherein said ballast comprises an active component of said imaging device.

11. The device as in claim 1, comprising a first optical system facing parallel to an axial direction and a second optical system facing perpendicular to said axial direction.

12. The device of claim 1, wherein said ballast is positioned around said window.

13. The device of claim 1, comprising an optical system located on a transverse side of said in-vivo device displaced from said longitudinal axis of symmetry.

14. The device of claim 13, wherein said optical system comprises a magnifying device.

15. The device of claim 1, wherein said window is on a side of said device on the longitudinal axis of symmetry.

16. The device of claim 1, wherein said window is on a side of said device transverse to the longitudinal axis of symmetry.

17. An in vivo imaging device comprising: a housing having a longitudinal axis of symmetry:
a first imager and first optical system in said housing to image in a direction parallel to an axial portion of said in vivo imaging device;
a second imager and second optical system in said housing to image in a direction parallel to a transverse portion of said imaging device; and
a ballast located off the longitudinal axis of symmetry of the housing, wherein said device has a center of gravity displaced from the longitudinal axis of symmetry in the direction of an in vivo area being imaged, such that the device rests in a known orientation.

18. The device as in claim 17, comprising a curved mirror.

19. The device as in claim 17, wherein said second optical system is configured to direct light reflected from a circular field of view.

20. The device as in claim 17, wherein said second optical system is configured to direct light reflected off a ring shaped slice of an in-vivo area.

21. The device as in claim 13, wherein:
said first optical system is configured to collect light reflected from a first in-vivo area in front of said axial portion of said device; and
said second optical system is configured to collect light reflected from a second in-vivo area parallel to said transverse portion of said imaging device.

22. The device as in claim 17, comprising a transmitter to transmit image data collected by said first and second imagers.

23. The device as in claim 22, wherein said transmitter is configured to transmit said data on more than one channel.

24. The device as in claim 17, wherein said device is configured to be swallowed.

25. The device as in claim 17, wherein said second optical system is configured to capture light from a field of view of at least 180 degrees.

26. The device as in claim 17, wherein said second optical system comprises a magnifying lens.

27. The device as in claim 17, wherein said second optical system comprises a transparent ring-shaped shell.

28. The device of claim 17, wherein said second imager is positioned to image an in vivo area through a window in said imaging device.

29. The device of claim 28, wherein said ballast is positioned around said window.

30. The device of claim 17, comprising an optical system located on a transverse side of said in-vivo device displaced from said longitudinal axis of symmetry.

31. The device of claim 30, wherein said optical system comprises a magnifying device.

32. A method of in vivo imaging, comprising: orienting an autonomous in-vivo imaging device with a ballast, wherein said device has a housing having a longitudinal axis of symmetry with said ballast being located off the longitudinal axis of symmetry and causing a center of gravity of the device to be displaced from the longitudinal axis of symmetry in the direction of an in vivo area to be imaged, such that the device rests in a known orientation; and
- capturing an image of an in-vivo area perpendicular to the longitudinal axis of symmetry of the device, wherein said ballast is on substantially the same side of the longitudinal axis of the device as the in vivo area imaged.

33. The method as in claim 32, comprising moving a body wherein said device is located.

34. The method as in claim 32, wherein said capturing comprises capturing an image of an area surrounding a transverse portion of said device.

35. The method as in claim 32, comprising positioning a body wherein said device is located.

* * * * *

UNITED STATES PATENT AND TRADEMARK OFFICE
CERTIFICATE OF CORRECTION

PATENT NO.          : 7,553,276 B2
APPLICATION NO.  : 10/812908
DATED                    : June 30, 2009
INVENTOR(S)         : Gavriel J. Iddan It is certified that error appears in the above-identified patent and that said Letters Patent is hereby corrected as shown below:

Col. 9, Line 36-43, should read:

Claim 1. An autonomous in-vivo device comprising:

a housing having a longitudinal axis of ~~symmetry:~~ symmetry;

an image sensor positioned in said housing to acquire images through a window in said housing; and a ballast located off the longitudinal axis of symmetry, so that said device has a center of gravity displaced from the longitudinal axis of symmetry toward said window, such that the device rests in a known orientation.

Col. 10, Line 15-27, should read:

Claim 17. An in vivo imaging device comprising:

a housing having a longitudinal axis of ~~symmetry:~~ symmetry;

a first imager and first optical system in said housing to image in a direction parallel to an axial portion of said in vivo imaging device;

a second imager and second optical system in said housing to image in a direction parallel to a transverse portion of said imaging device; and a ballast located off the longitudinal axis of symmetry of the housing, wherein said device has a center of gravity displaced from the longitudinal axis of symmetry in the direction of an in vivo area being imaged, such that the device rests in a known orientation.

UNITED STATES PATENT AND TRADEMARK OFFICE
CERTIFICATE OF CORRECTION

| | |
|---|---|
| PATENT NO. | : 7,553,276 B2 |
| APPLICATION NO. | : 10/812908 |
| DATED | : June 30, 2009 |
| INVENTOR(S) | : Gavriel J. Iddan |

It is certified that error appears in the above-identified patent and that said Letters Patent is hereby corrected as shown below:

Col. 10, Line 35, should read:

Claim 21. The device as in claim ~~13~~ 17, wherein:

Signed and Sealed this

Fifteenth Day of December, 2009

David J. Kappos
*Director of the United States Patent and Trademark Office*